(12) United States Patent
Faizan et al.

(10) Patent No.: US 11,751,783 B2
(45) Date of Patent: Sep. 12, 2023

(54) SYSTEM AND METHOD FOR MENTAL STATE DETERMINATION

(71) Applicant: Mirza Faizan, Irving, TX (US)

(72) Inventors: Mirza Faizan, Irving, TX (US); Vineet Anshuman, Sunnyvale, CA (US); Sidra Ambreen, Plano, TX (US); Binu Kurien Varghese, Glandale, CA (US); Syed Shah Ekramullah Alvi, Irving, TX (US); Abdul Malik Ayam, Irving, TX (US); Hunzalah Iqbal, Matthews, NC (US); Mustafa Qadri, Irving, TX (US); Ayan Zaman, Irving, TX (US); Mirza Rizwan, Patna (IN); Ridah Shaista Shanavas, Hyderabad (IN); Saadia Asaf, Aligarh (IN); Mansoor Hasan Khan, Aligarh (IN)

( * ) Notice: Subject to any disclaimer, the term of this patent is extended or adjusted under 35 U.S.C. 154(b) by 197 days.

(21) Appl. No.: 17/339,205

(22) Filed: Jun. 4, 2021

(65) Prior Publication Data
US 2022/0386914 A1    Dec. 8, 2022

(51) Int. Cl.
| A61B 5/00 | (2006.01) |
| A61B 5/145 | (2006.01) |
| A61B 5/16 | (2006.01) |
| G16H 15/00 | (2018.01) |
| G16H 40/63 | (2018.01) |
| A61B 5/1477 | (2006.01) |

(52) U.S. Cl.
CPC ............ *A61B 5/165* (2013.01); *A61B 5/1477* (2013.01); *A61B 5/14517* (2013.01); *A61B 5/14546* (2013.01); *A61B 5/7246* (2013.01); *A61B 5/742* (2013.01); *G16H 15/00* (2018.01); *G16H 40/63* (2018.01)

(58) Field of Classification Search
CPC ..... A61B 5/165; A61B 5/14517; A61B 5/145; A61B 5/1455; A61B 5/14546; A61B 5/1477; A61B 5/7246; A61B 5/742; A61B 5/681
See application file for complete search history.

(56) References Cited

U.S. PATENT DOCUMENTS

| 7,720,784 | B1 * | 5/2010 | Froloff | A61B 5/165 600/300 |
| 11,479,258 | B1 * | 10/2022 | Sanchez | A61B 5/746 |
| 2002/0086343 | A1 * | 7/2002 | Cameron, Sr. | C12Y 301/01007 435/20 |
| 2017/0100072 | A1 * | 4/2017 | Heikenfeld | A61B 5/1477 |
| 2018/0035927 | A1 * | 2/2018 | Cronin | A61B 5/14517 |

* cited by examiner

*Primary Examiner* — Chu Chuan Liu

(57) ABSTRACT

The invention relates to mental health and using technology that can analyze and interpret hormones from drops of sweat and also a peer to peer feedback system to predict mental health issues (such as depression) in an individual. The invention further relates to the monitoring of sweat and feedback and interpreting the two in tandem to identify symptoms of mental health illnesses in an individual over a period of time (to predict and prevent that certain mental health disease). Furthermore, the records of the sweat analysis and peer to peer feedback will be utilized to provide smart suggestions and track the mental health of an individual.

9 Claims, 4 Drawing Sheets

SYSTEM AND METHOD FOR MENTAL STATE DETERMINATION

TECHNICAL FIELD

The invention relates to a wearable emergency medical device. More specifically, this device can be worn by the user as a medical bracelet device and relates to sweat analysis system to determine mental state of the user.

BACKGROUND OF THE INVENTION

Depression is an issue that can't be eradicated. But it is something that can be prevented if identified in its early stages. And that is what our innovation serves to do. Depression isn't something that can always be seen outright and explicitly and this is an issue. Many family members may realize too late that their loved one is suffering from this atrocity, and at that time too much damage may have been done. Depression is just an example, though. Many mental illnesses are like this in which signs and symptoms may be shown but it is hard to identify. And unadulterated exposure to such illnesses can lead to acts of drug abuse, harming self and others, deadly thoughts, and so much more.

Depression affects a lot of people across the globe and is a common problem that many people face on a daily basis. Health statistics show that almost 350 million people suffer from depression each year worldwide. Just in the U.S. around 43,000 adults commit suicide annually as a result of depression. About 18% of adults and approximately 10%-15% of adolescents face depression. This costs the U.S government $51 billion in combined medical and works loss costs annually. Depression has also been another leading cause of people becoming alcoholic and drug addicts. Depression is a mental health issue affecting people globally not limited to just people of a specific area, profession, or ethnicity. Anyone who is subjected to too much stress and when they don't know how to handle it, they are prone to be impacted by this disorder.

Thus, there is an unmet need for a device which can solve the above mentioned drawback and to tackle the growing medical issue.

SUMMARY OF THE INVENTION

The present invention discloses a system for mental state determination, said system configured to determine one or more hormone levels extracted from sweat of a user; a peer to peer feedback system configured to generate a report based on one or more behavioral aspects of said user; a memory unit configured to store said determined one or more hormone levels by said sweat analysis system and said generated report; and a computation unit configured to determine a mental state of said user by computing output of said sweat analysis system and output of said peer to peer feedback system.

In an embodiment of the present invention, a method for sweat analysis for determining the mental state is provided, said method comprising steps of: determining one or more hormone levels extracted from sweat of a user; generating a report based on one or more behavioral aspects of said user; storing said determined one or more hormone levels by said sweat analysis system and said generated report; and determining a mental state of said user by computing output of said sweat analysis system and output of said peer to peer feedback system.

OBJECTIVE OF INVENTION

The objective of the disclosed invention is to have the ability to identify medical emergencies in relation to depression.

Yet another objective of the invention is to help an individual who is probably facing a depression or going through depression by providing the user with tips on how to improve their mood based on their location and time.

Yet another objective of the invention is to trace the affected person by tracking the location of the smartphone to locate the position of the user at any given time and based on his/her interests it will suggest some activities that he/she can do to improve his/her mood.

Yet another objective of the present invention is that if a user is in need of medical attention this will notify paramedics or surrounding people.

Yet another objective of the invention is to communicatively transmit the medical records, and measured vitals in case of abnormal activity to emergency contacts and the medical staff.

BRIEF DESCRIPTION OF THE DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not to limit the scope in any manner, wherein like designations denote similar elements, and in which.

DETAILED DESCRIPTION OF DRAWINGS

Figure 1A:
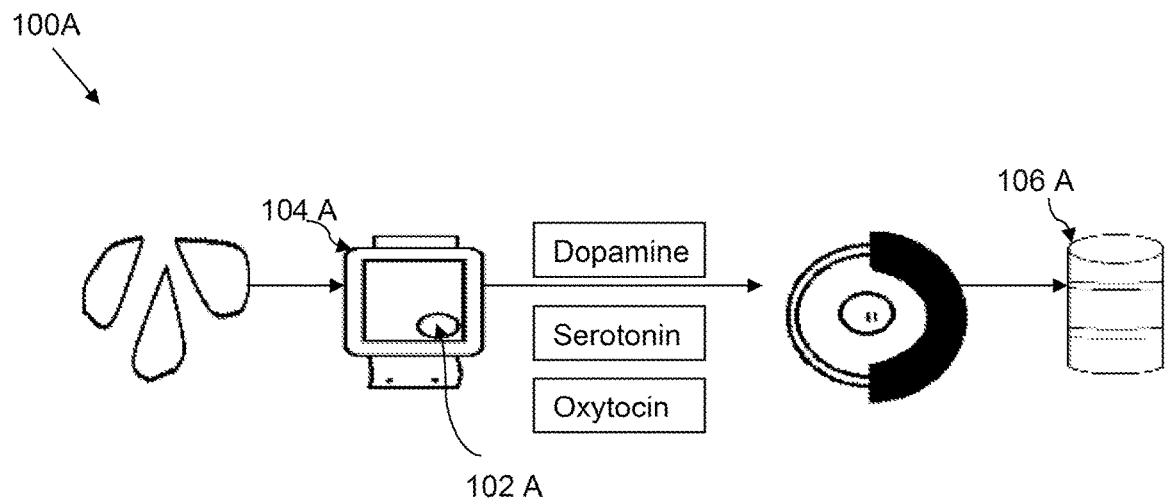
FIG. 1A is an exemplary sweat analysis system in which various embodiments may be implemented.

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "an embodiment," "at least one embodiment," "one example," "an example," "for example," and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

Definitions: The following terms shall have, for the purposes of this application, the respective meanings set forth below.

A "computing device" refers to a device that includes one or more processors/microcontrollers and/or any other electronic components, or a device or a system that performs one or more operations according to one or more programming instructions/codes. Examples of a computing device may include, but are not limited to, a desktop computer, a laptop, a personal digital assistant (PDA), a mobile device, a smartphone, a tablet computer (e.g., iPad®, and Samsung Galaxy Tab®), and the like.

A "patient or a user" is a human being who may require medical care or treatment by a medical expert, such as a doctor. In other words, a patient is a recipient of health care services provided by a health practitioner. In an embodiment, a patient refers to a patient who is currently under medical observation and who may be suffering from mental depression.

An "electronic medical record" refers to a documentation of health condition of a patient. In an embodiment, the medical record may include periodic measures of physiological parameters associated with the patient. Further, the medical record may include nursing notes documented over a specific time by a healthcare professional (such as a doctor, a nurse, a medical attender, a hospital staff, and/or the like). In an embodiment, the nursing notes may include recorded observations, administered drugs and therapies, test results, X-rays, nursing reports, investigative reports, and the like. In an embodiment, the medical record may be documented on a computing device, such as, but not limited to, a desktop computer, a laptop, a PDA, a mobile device, a smartphone, a tablet computer (e.g., iPad® and Samsung Galaxy Tab®), and the like. In an embodiment, the medical record may correspond to electronic or handwritten document(s).

A "sensor" refers to a device that detects/measures events or changes in quantities and provides a corresponding output, generally as an electrical or optical signal. In healthcare domain, a first type of sensors may be operable to detect and measure various biological and physical variations corresponding to the patient. Such detected and measured signals may be recorded for further analytics. For example, biomedical sensors are used to monitor heart rate, respiration rate, pulse rate, blood pressure, and the like, of the first patient. Further, sensors may be operable to detect and measure various physical and/or chemical signals corresponding to a medical device associated with the patient. For example, pressure sensors, temperature sensors, and humidity sensors are used to monitor and regulate gas flow and gas conditions in anesthesia machines, respirators, and ventilators. The sensor may be an acceleration sensor or a vibration sensor, such as a VTT or TI standard chip base accelerometer. These examples are currently contemplated, but it should be understood that alternatives exist.

A "wearable device" refers to a device which may be easily worn by a user. The user may wear the wearable device at a plurality of body parts and not necessarily a wrist of the user.

FIG. 1A is an exemplary sweat analysis system in which various embodiments may be implemented.

As shown in FIG. 1A, the exemplary sweat analysis system 100A, comprises a sensor 102A, that may be embedded in a wrist band 104A, a hormone level database 106A. The sensor 102A may be configured to determine presence of Oxytocin, Dopamine and Serotonin in the sensed element. The sensed element may be drop of sweat.

Furthermore, the sweat analysis system consists of a sensor that may scan a drop of sweat and read the levels of the hormones that are released in it. For AR, the sensor 102A may be scanning for 3 specific hormones: Oxytocin, Dopamine and Serotonin. The readings of these hormone levels may be used to determine mood at any given time and place.

The determined real time data (hormone level readings) are then transmitted wirelessly to be used by the processor on the smartphone. As long as the person is wearing the band, the data may be sent to the processor at a remote location and may be retained for a period of time for analysis as required.

Figure 1B:
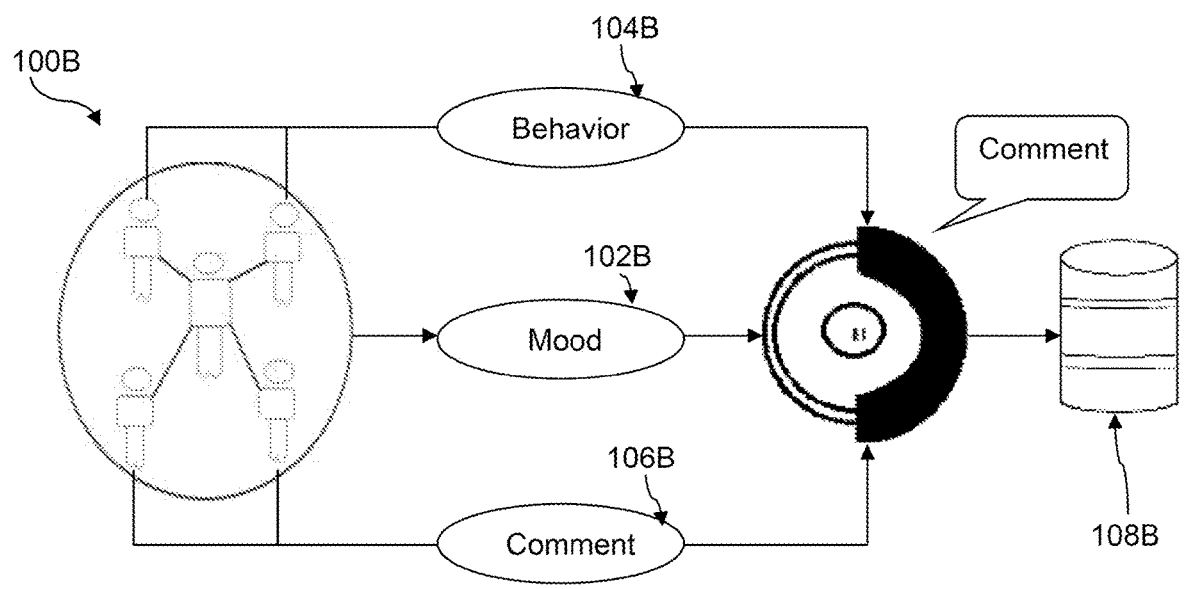
FIG. 1B is an exemplary peer to peer feedback system in which various embodiments may be implemented.

FIG. 1B is an exemplary peer to peer feedback system in which various embodiments may be implemented.

As shown in FIG. 1B, the peer-to-peer feedback system 100B comprises a mood determination unit 102B, a behavior determination unit 104B, comments capturing unit 106B, and a feedback database 108B.

The mood determination unit 102B may be configured to determine mood of the user under observation by peers in the network. Furthermore, the mood determination unit 102B may further comprise one or more specific features for mentioning the mood of the user.

The behavior determination unit 104B may be configured to determine behave of the user under observation by peers in the network. Furthermore, the behavior determination unit 104B may further comprise one or more specific features for mentioning the mood of the user.

The comments capturing unit 106B may be configured to capture plurality of comments given by the peers in the network. Furthermore, each of the comments may be auto corrected in proper format for processing. The keywords may be determined by the processor to provide an output to the peer-to-peer feedback system and thereafter to the final processing system.

In an embodiment of the present invention, using this system isn't limited to peers and friends of the person, rather anyone in his social network can rate and give feedback on the person's behaviour. Hence, people can review the behavior, if the user was acting normally or not and comment on their interaction with the user. All this peer to peer feedback data may be captured by the processor.

Figure 1C:
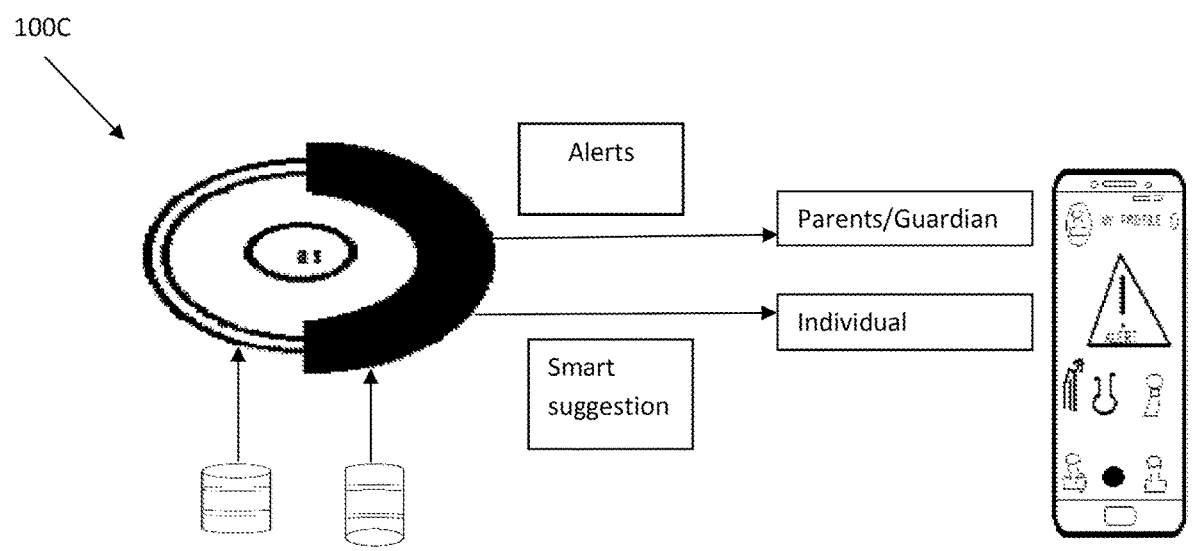
FIG. 1C is an exemplary computation system in which various embodiments may be implemented.

FIG. 1C is an exemplary computation system 100C in which various embodiments may be implemented.

The data collected from the peer to peer feedback system and sweat analysis system may be stored by the processor in a database. Then the processor may correlate both these data to determine if the user is indeed suffering from depression. Everyone using AR may be required to download software on his/her smartphone and has to provide details like guardian/contact information, places of interest, etc during their profile creation.

In an embodiment, the processor may be configured internally to send alerts to this guardian/contact person of the user when it detects a potential case of depression. Not only with this historical data from both the systems does AR help to predict and stop depression at early stages but also can be used to track the progress a depressed individual is making for the treatment that he/she has been receiving.

In an exemplary embodiment, a wearable medical emergency detection device may be a bracelet. In an embodiment the wearable device may be worn on the wrist. The bracelet consists of a wristband that has houses the entire system as disclosed in FIGS. 1A, 1B, and 1C. Alternate examples of wearable device forms include, but are not limited to, necklaces, rings, pin-on items, belts, watches, belt attachments, chest bands, items capable of being carried in a pocket, and articles of clothing.

In an embodiment of the present invention, a top face of the wearable medical emergency detection device may be made of a touch screen. In an embodiment the touch screen may be configured to display one or more information such as real time data, vitals, and the alike.

In a further embodiment of the present invention, the touch screen may also display one or more notifications, such notification may include an emergency notification, an incoming message notification.

In an embodiment, the entire system may also communicate audibly using audio codec, which may receive spoken information from a user and convert it to usable digital information. Audio codec may likewise generate audible sound for a user, such as through a speaker, e.g., in a handset of device. Such sound may include sound from voice telephone calls, may include recorded sound (e.g., voice messages, music files, etc.) and may also include sound generated by applications operating on device.

In an embodiment, the wearable medical emergency detection device may include a power unit. The power unit may include one or more batteries. The one or more batteries may be solar enabled chargeable batteries. The chargeable batteries may provide power of each and every unit of the wearable medical emergency detection device.

In an embodiment, the device may include a memory chip to store information. The memory may stores information within the device 100. In one implementation, the memory is a volatile memory unit or units. In another implementation, the memory is a non-volatile memory unit or units. The memory may also be another form of computer-readable medium, such as a magnetic or optical disk. The memory may store the medical records, personal data of the user.

The memory is capable of providing mass storage for the device 100. In one implementation, the memory may be or contain a computer-readable medium, such as a floppy disk device, a hard disk device, an optical disk device, a tape device, a flash memory or other similar solid state memory device, or an array of devices, including devices in a storage area network or other configurations.

In an embodiment, the device may include a Bluetooth transmitter and receiver to send and receive limited amounts of information. Device 100 may communicate wirelessly through communication interface, which may include digital signal processing circuitry where necessary. Communication interface may provide for communications under various modes or protocols, such as GSM voice calls, SMS, EMS, or MMS messaging, CDMA, TDMA, PDC, WCDMA, CDMA2000, or GPRS, among others.

Such communication may occur, for example, through radio-frequency transceiver. In addition, short-range communication may occur, such as using a Bluetooth, Wi-Fi, or other such transceiver (not shown). In addition, GPS (Global Positioning System) receiver module may provide additional navigation- and location-related wireless data to device 100, which may be used as appropriate by applications running on device 100.

In an embodiment, the device 100 may include a NFC chip to send all information, GPS system to find location. In an alternate embodiment, the device may be communicatively connected with the wireless communication technology.

In an embodiment, the device 100 may include a micro processing unit to act on given values, is located inside the device. The micro processing unit may be configured to determine various colors of emergency.

Figure 2:
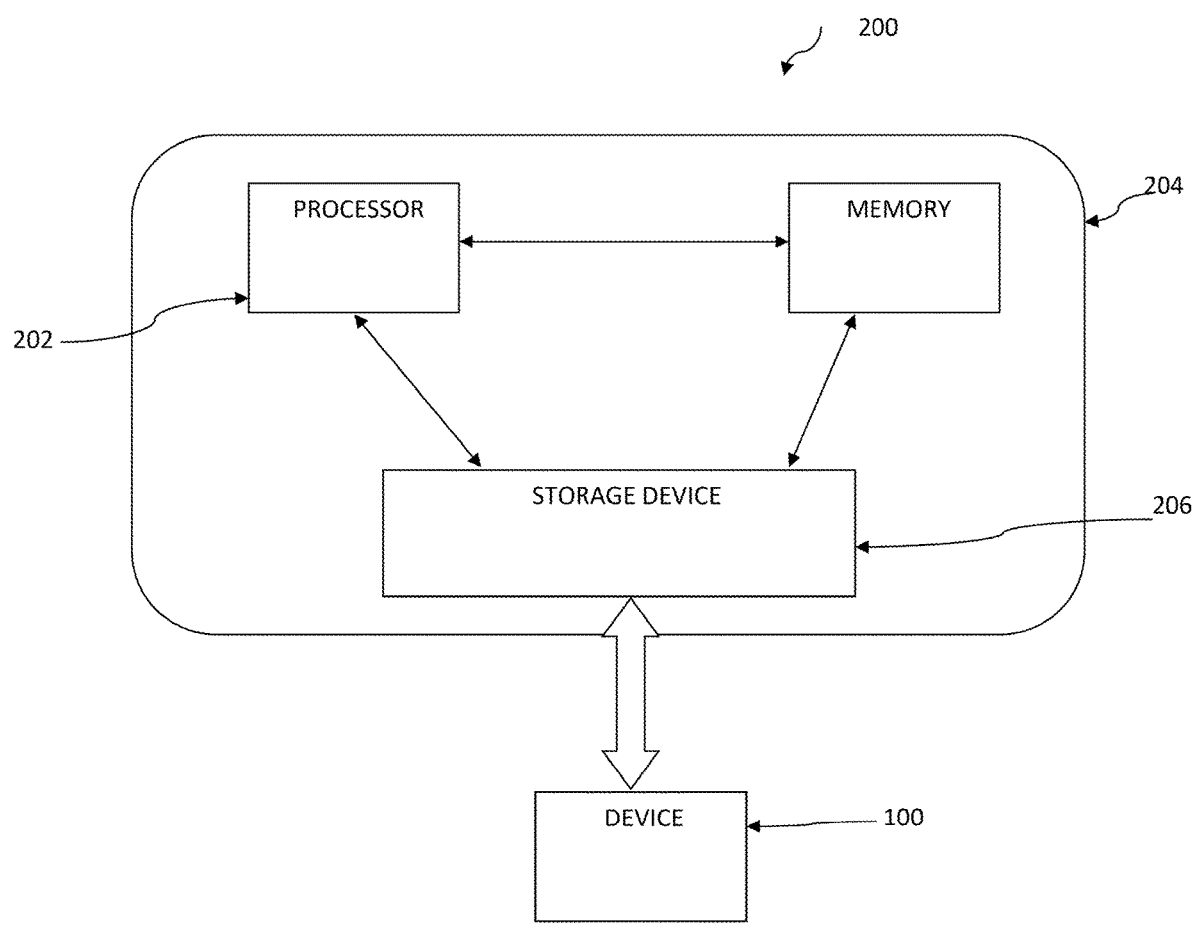
FIG. 2 is a block diagram illustrating a system environment in which various embodiments may be implemented.

FIG. 2 shows an example of a computing device 200 and a device 100 that can be used to implement the techniques described here. Computing device 200 is intended to represent various forms of digital computers, such as laptops, desktops, workstations, personal digital assistants, servers, blade servers, mainframes, and other appropriate computers. Computing device 200 is intended to represent various forms of mobile devices, such as personal digital assistants, cellular telephones, smartphones, and other similar computing devices. The components shown here, their connections and relationships, and their functions, are meant to be exemplary only, and are not meant to limit implementations described and/or claimed in this document.

Computing device 200 includes a processor 202, memory 204, a storage device 206, a high-speed interface connecting to memory 204 and high-speed expansion ports, and a low speed interface connecting to low speed bus and storage device 206. Each of the components 202, 204, 206 are interconnected using various busses, and may be mounted on a common motherboard or in other manners as appropriate. The processor 202 can process instructions for execution within the computing device 200, including instructions stored in the memory 204 or on the storage device 206 to display graphical information for a GUI on an external input/output device, such as display coupled to high speed interface. In other implementations, multiple processors and/or multiple busses may be used, as appropriate, along with multiple memories and types of memory. Also, multiple computing devices 200 may be connected, with each device providing portions of the necessary operations (e.g., as a server bank, a group of blade servers, or a multi-processor system).

The memory 204 stores information within the computing device 200. In one implementation, the memory 204 is a volatile memory unit or units. In another implementation, the memory 204 is a non-volatile memory unit or units. The memory 204 may also be another form of computer-readable medium, such as a magnetic or optical disk. The memory may also be a part of hardware housing unit 102.

The storage device 206 is capable of providing mass storage for the computing device. In one implementation, the storage device 206 may be or contain a computer-readable medium, such as a floppy disk device, a hard disk device, an optical disk device, a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 204, the storage device 206, or memory on processor 202.

The high-speed controller manages bandwidth-intensive operations for the computing device 200, while the low speed controller manages lower bandwidth-intensive operations. Such allocation of functions is exemplary only. In one implementation, the high-speed controller is coupled to memory 204, display (e.g., through a graphics processor or accelerator), and to high-speed expansion ports, which may accept various expansion cards (not shown). In the implementation, low-speed controller is coupled to storage device 206 and low-speed expansion port. The low-speed expansion port, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 200 may be implemented in a number of different forms, as shown in the figure. For example, it may be implemented as a standard server, or multiple times in a group of such servers. It may also be implemented as part of a rack server system. In addition, it may be implemented in a personal computer such as a laptop computer. Alternatively, components from computing device 200 may be combined with other components in a mobile device (not shown), such as device 100. Each of such devices may contain one or more of computing device 200, and an entire system may be made up of multiple computing devices 100, 200 communicating with each other.

The processor 202 can execute instructions within the computing device 200, including instructions stored in the memory 204. The processor may be implemented as a chipset of chips that include separate and multiple analog and digital processors.

Processor 202 may communicate with a user through control interface and display interface coupled to a display. The display may be, for example, a TFT LCD (Thin-Film-Transistor Liquid Crystal Display) or an OLED (Organic Light Emitting Diode) display, or other appropriate display technology. The display interface may comprise appropriate circuitry for driving the display to present graphical and other information to a user. The control interface may receive commands from a user and convert them for submission to the processor 202. In addition, an external interface may be provided in communication with processor 202, so as to enable near area communication of device 100 with other devices. External interface may provide, for example, for wired communication in some implementations, or for wireless communication in other implementations, and multiple interfaces may also be used.

The memory stores information within the computing device 200 or 100. The memory can be implemented as one or more of a computer-readable medium or media, a volatile memory unit or units, or a non-volatile memory unit or units. Expansion memory may also be provided and connected to device 200 through expansion interface, which may include, for example, a SIMM (Single In Line Memory Module) card interface. Such expansion memory may provide extra storage space for device 200/100, or may also store applications or other information for device 100/200. Specifically, expansion memory may include instructions to carry out or supplement the processes described above, and may include secure information also. Thus, for example, expansion memory may be provide as a security module for device 100, and may be programmed with instructions that permit secure use of device 100. In addition, secure applications may be provided via the SIMM cards, along with additional information, such as placing identifying information on the SIMM card in a non-hackable manner.

The memory may include, for example, flash memory and/or Non VolatileRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory, expansion memory, or memory on processor.

Device 100 may communicate wirelessly through communication interface, which may include digital signal processing circuitry where necessary. Communication interface may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver. In addition, short-range communication may occur, such as using a Bluetooth, Wi-Fi, or other such transceiver (not shown). In addition, GPS (Global Positioning System) receiver module may provide additional navigation- and location-related wireless data to device 100, which may be used as appropriate by applications running on device 100.

Device 100 may also communicate audibly using audio codec, which may receive spoken information from a user and convert it to usable digital information. Audio codec may likewise generate audible sound for a user, such as through a speaker, e.g., in a handset of device 100. Such sound may include sound from voice telephone calls, may include recorded sound (e.g., voice messages, music files, etc.) and may also include sound generated by applications operating on device 100.

The computing device 200 may be implemented in a number of different forms, as shown in the figure. For example, it may be implemented as a cellular telephone. It may also be implemented as part of a smartphone, personal digital assistant, or other similar mobile device.

Additionally computing device 200 or device 100 can include Universal Serial Bus (USB) flash drives. The USB flash drives may store operating systems and other applications. The USB flash drives can include input/output components, such as a wireless transmitter or USB connector that may be inserted into a USB port of another computing device.

Figure 3:
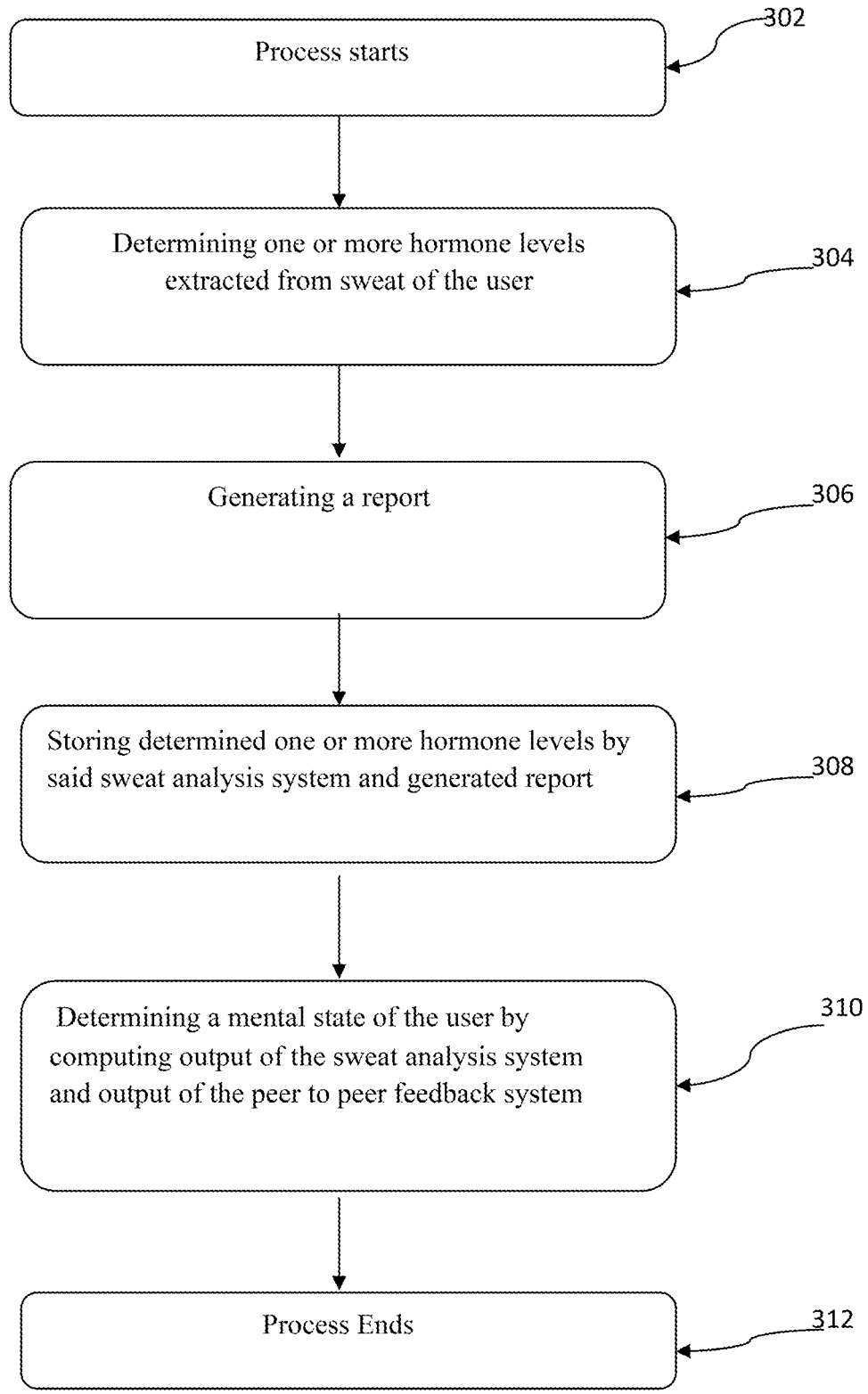
FIG. 3 is a flowchart illustrating a method for abjection redirection, in accordance with at least one embodiment.

FIG. 3 is a flowchart a method for mental state determination and notify, in accordance with at least one embodiment. With reference to FIG. 3, there is shown a flowchart 300 that is described in conjunction with FIGS. 1A, 1B, 1C and 2. The method starts at step 302 and proceeds to step 304.

At step 304 one or more hormone levels extracted from sweat of the user are determined. In an embodiment, the sensor 102 may be configured to sense the one or more hormone levels extracted from sweat of the user.

At this step, the sweat analysis system consists of a sensor that may scan a drop of sweat and read the levels of the hormones that are released in it. For AR, the sensor 102A may be scanning for 3 specific hormones: Oxytocin, Dopamine and Serotonin. The readings of these hormone levels may be used to determine mood at any given time and place.

After this, the determined real time data (hormone level readings) are then transmitted wirelessly to be used by the processor on the smartphone. As long as the person is wearing the band, the data may be sent to the processor at a remote location and may be retained for a period of time for analysis as required.

At step 306 a report may be generated. The processor may be configured to generate a report based on one or more behavioral aspects. The generated report may be in any form of data available in the open source market.

The peer to peer feedback system 100B may be configured to determine the one or more behavioral aspects of the user. In an embodiment, the mood determination unit 102B may be configured to determine mood of the user under observation by peers in the network. Furthermore, the mood determination unit 102B may further comprise one or more specific features for mentioning the mood of the user.

The behavior determination unit 104B may be configured to determine behave of the user under observation by peers in the network. Furthermore, the behavior determination unit 104B may further comprise one or more specific features for mentioning the mood of the user.

The comments capturing unit 106B may be configured to capture plurality of comments given by the peers in the network. Furthermore, each of the comment may be auto corrected in proper format for processing. The keywords may be determined by the processor to provide an output to the peer to peer feedback system and thereafter to the final processing system. The entire information may be stored in feedback database 108B.

At step 308 storing said determined one or more hormone levels by said sweat analysis system and said generated report. After the execution of step 304, and 306, the determined one or more hormone levels by the sweat analysis system and the generated report may be stored. The storage of data may be temporary or may be permanent in nature. Furthermore, the stored information may be transmitted wirelessly to a remote location.

At step 310 determining a mental state of the user by computing output of the sweat analysis system and output of the peer to peer feedback system. In an embodiment, the processor may be configured to determine the mental state of the user. The mental state may be determined based on computation of data that may be captured by the sweat analysis system and output of the peer to peer feedback system. The process ends at step 312.

Further, if the bracelet is connected through Bluetooth connection to the user's phone, it can automatically call emergency services, and read off the user's medical information, as well as approximate location (taken through the bracelet's GPS system). The bracelet will also send out messages to everyone in close proximity through Bluetooth sharing capabilities, which will display a very basic version of the patient's medical history and how to perform first aid on the patient.

In an alternate embodiment, the Bracelet may be made from different materials. The different materials may be a combination of metal and polymer materials. The bracelet may be adjustable with an open portion adapted to fit on one or more inner portions of a user's wrist. Other materials and combinations of materials, including precious metals and gems so that the bracelet functions as jewelry. Some examples may be designed for style and/or fashion to have a subjectively attractive external appearance. Furthermore, the Bracelet may be flexible and/or may be abrasion resistant and/or UV stable.

In an embodiment of the present invention, the disclosed system further provides a suggestion unit. The suggestion unit may be configured to suggest one or more activities. The suggestion of activities may be based on plurality of attributes. The attributes may be a time, a location, preferences of the user, and alike. Furthermore, based on this, the system may communicate push message suggesting an activity to perform by the user. The activity may be for example but not limited to watching movie, playing games, talking to friends.

In a further embodiment, the functional components of bracelet are illustrated as being embedded in or otherwise integrated into the bracelet, other methods for securing or attaching some or all of the components should be possible, including external attachments and making the body of bracelet hollow to permit internal mounting of components.

In an embodiment, the device may include a transmitter that may be a standard use 915 mHz, 2.4 GHz, or 6.0 Ghz transmitter of any type commonly used in wireless phone applications.

A chipset firmware can be suitably programmed or encoded to coordinate the interaction of fall sensor and transmitter. While a chipset is illustrated as the device for effecting and controlling the functionality of bracelet, alternatives and equivalents including, but not limited to, other types of controller, software, hardware, and/or firmware may be suitable.

In an exemplary embodiment, the device 100 may also be provided with a vibration feature. When a pre-defined vibration pattern is generated then at such instance the user device may send a notification to emergency contact and medical staffs. In an alternate embodiment, on detecting such a specific vibration pattern, the nearby people may also be notified. This may further provide the wearer an opportunity to cancel the alert signal, for example with another press of button, in case the activation was accidental.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. Moreover, other mechanisms for performing the systems and methods described in this document may be used. In addition, the logic flows depicted in the figures may not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A mental state determination system, said system comprising:
    a first set of sensors configured to determine one or more hormone levels extracted from sweat of a first user;
    a processor configured to:
    determine one or more behavioral aspects of said first user based on feedback from a network of second users about said first user, wherein said first user is included in said network of second users;
    generate a first report based on said one or more behavioral aspects of said first user; and
    determine a mental state of said first user based on said one or more hormone levels and said first report.

2. The system as claimed in claim 1, wherein said hormones are at least Oxytocin, Dopamine, and Serotonin.

3. The system as claimed in claim 1, further comprising a second set of sensors configured to sense one or more physical values of body of said first user.

4. The system as claimed in claim 1, further comprising a display screen.

5. The system as claimed in claim 1, wherein said processor is further configured to suggest one or more activities based on one or more attributes.

6. The system as claimed in claim 1, wherein said mental state determination system is embedded in a wearable device.

7. A method for determination of mental state, said method comprising steps of:
    determining one or more hormone levels extracted from sweat of a first user;
    determining one or more behavioral aspects of said first user based on feedback from a network of second users, wherein said first user is included in said network of second users;
    generating a report based on said one or more behavioral aspects of said first user; and
    determining a mental state of said first user based on said one or more hormone levels and said report.

8. The system as claimed in claim 1, wherein
    said processor is further configured to generate a second report that indicates a mental wellness index of said first user, and
    said second report is generated based on the feedback from the network of second users about said first user.

9. The system as claimed in claim 1, wherein said processor is further configured to generate a personality score for said first user based on the feedback from the network of second users about said first user.

* * * * *